US008404850B2

(12) United States Patent  
Cabell et al.

(10) Patent No.: US 8,404,850 B2
(45) Date of Patent: Mar. 26, 2013

(54) BIS-QUATERNARY PYRIDINIUM-ALDOXIME SALTS AND TREATMENT OF EXPOSURE TO CHOLINESTERASE INHIBITORS

(75) Inventors: Larry Allen Cabell, San Antonio, TX (US); Joseph A McDonough, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 833 days.

(21) Appl. No.: 12/047,988

(22) Filed: Mar. 13, 2008

(65) Prior Publication Data

US 2009/0281144 A1 Nov. 12, 2009

(51) Int. Cl.
C07D 213/00 (2006.01)
A61K 31/44 (2006.01)
(52) U.S. Cl. ........................................ 546/264; 514/332
(58) Field of Classification Search .................. None
See application file for complete search history.

(56) References Cited

U.S. PATENT DOCUMENTS

| | | | |
|---|---|---|---|
| 2,305,947 A | 8/1942 | Armstrong et al. |
| 2,305,917 A | 12/1942 | Armstrong |
| 2,816,113 A | 12/1957 | Wilson |
| 3,135,761 A | 6/1964 | Hackley et al. |
| 3,137,702 A | 6/1964 | Luttringhaus et al. |
| 3,629,425 A | 12/1971 | Hussain |
| 3,929,813 A | 12/1975 | Higuchi et al. |
| 4,128,651 A | 12/1978 | Hagedorn |
| 4,305,947 A | 12/1981 | Bartner |
| 4,540,602 A | 9/1985 | Motoyama et al. |
| 4,705,777 A | 11/1987 | Lehrer et al. |
| 4,880,610 A | 11/1989 | Constantz |
| 5,130,438 A | 7/1992 | Hsiao et al. |
| 5,145,684 A | 9/1992 | Liversidge et al. |
| 5,298,504 A | 3/1994 | Sommer et al. |
| 5,589,167 A | 12/1996 | Cleland |
| 5,662,883 A | 9/1997 | Bagchi et al. |
| 5,716,642 A | 2/1998 | Bagchi et al. |
| 5,770,181 A | 6/1998 | Kirkland |
| 5,902,816 A * | 5/1999 | Viner .......................... 514/334 |
| 5,929,093 A * | 7/1999 | Pang et al. .................... 514/332 |
| 6,007,845 A | 12/1999 | Domb et al. |
| 6,117,454 A | 9/2000 | Kreuter et al. |
| 6,355,271 B1 | 3/2002 | Bell et al. |
| 6,395,029 B1 | 5/2002 | Levy et al. |
| 6,656,505 B2 | 12/2003 | Kundu et al. |
| 6,815,543 B1 | 11/2004 | Bernardelli |
| 6,861,068 B2 | 3/2005 | Ng et al. |
| 6,881,745 B2 | 4/2005 | Hayes et al. |
| 7,037,528 B2 | 5/2006 | Kipp et al. |
| 7,081,161 B2 | 7/2006 | Genge et al. |
| 7,282,194 B2 | 10/2007 | Sung et al. |
| 7,300,670 B2 | 11/2007 | Venus et al. |
| 7,387,792 B2 | 6/2008 | Hirsh et al. |
| 7,390,384 B2 | 6/2008 | Fang et al. |
| 2003/0073619 A1 | 4/2003 | Mahato et al. |
| 2004/0022820 A1 | 2/2004 | Anderson |
| 2004/0256749 A1 | 12/2004 | Chaubal et al. |
| 2004/0266502 A1 | 12/2004 | Kipp et al. |
| 2005/0106257 A1 | 5/2005 | Albayrak |
| 2005/0113489 A1 | 5/2005 | Baran, Jr. et al. |
| 2005/0118108 A1 | 6/2005 | Cowan et al. |
| 2005/0202093 A1 | 9/2005 | Kohane et al. |
| 2005/0220888 A1 | 10/2005 | Putcha et al. |
| 2006/0063662 A1 | 3/2006 | Hata et al. |
| 2006/0183777 A1 | 8/2006 | Huang et al. |
| 2006/0216353 A1 | 9/2006 | Liversidge et al. |
| 2007/0093518 A1 | 4/2007 | Wetherell et al. |
| 2007/0134339 A1 | 6/2007 | Jenkins et al. |
| 2007/0190160 A1 | 8/2007 | Turos et al. |
| 2008/0145439 A1 | 6/2008 | Lobl et al. |
| 2008/0241256 A1 | 10/2008 | Kuhn |
| 2009/0263491 A1 | 10/2009 | Kreuter et al. |
| 2009/0304720 A1 | 12/2009 | Kreuter et al. |

FOREIGN PATENT DOCUMENTS

| | | |
|---|---|---|
| EP | 1319400 | 6/2003 |
| WO | 9814587 | 4/1998 |
| WO | 9841188 | 9/1998 |
| WO | 0163362 | 8/2001 |
| WO | 0232402 | 4/2002 |
| WO | 2004073033 | 8/2004 |
| WO | 2005123581 | 12/2005 |
| WO | 2007/001355 A2 | 1/2007 |
| WO | 2007/084460 A2 | 7/2007 |
| WO | 2009114298 | 9/2009 |

OTHER PUBLICATIONS

Radic, et al., "Evaluation of HI-6 oxime: potential use in protection of human acetylcholinesterase inhibited by antineoplastic drug irinotecan and its cyto/genotoxicity in vitro," Acta Biochimica Polonica vol. 54 No. 3/2007, 583-593, Aug. 23, 2007.
Stojiljkovic, et al., "Pryidinum Oximes: Rationale for their Selection as casual Antidotes against Organophosphate Poisonings and current solutions for auto-injectors," Arh Hig Toksikol 2006, 57:435-443.
Digiovanni, Jr., M.D., Cleto, Domestic Terrorism With Chemical or Biological Agents: Psychiatric Aspects, Am J Psychiatry, Oct. 1999, pp. 1500-1505, vol. 156:10.
D'Mello, G.D., Behavioural Toxicity of Anticholinesterases in Humans and Animals—A Review, Human & Experimental Toxicology, 1993, pp. 3-7, vol. 12.
Eyer, et al., Oximes—Chapter 15, Chemical Warfare Agents: Toxicology and Treatment, 2007, pp. 305-329, 2nd Edition.
Jager, et al., Toxicity of Diacetyl Monoxime and of Pyridine-2-Aldoxime Methiodide in Man, Bull John Hopkins Hosp., 1958, pp. 203-211, vol. 102.
Jamal, Goran A., Long term neurotoxic effects of organophosphate compounds, Adverse Drug React. Toxicol. Rev, 1995, pp. 85-99, vol. 14(2).
Marrs et al., Chemical Warfare Agents: Toxicology and Treatment Second Edition, 2007, pp all. Table of contents attached electronically, physical book is cited and supplied in U.S. Appl. No. 12/702,095 which was mailed to USPTO Oct. 8, 2010.

(Continued)

*Primary Examiner* — Joseph K. McKane
*Assistant Examiner* — Nyeemah A Grazier
(74) *Attorney, Agent, or Firm* — Grossman, Tucker et al

(57) ABSTRACT

Bis-quaternary pyridinium-aldoxime salts are disclosed, and their associated polymorphic character, along with their methods of preparation. Such polymorphic salts may then be used for treatment of exposure to cholinesterase inhibitors, such as a phosphorous containing cholinesterase inhibitor type compound.

22 Claims, 10 Drawing Sheets

OTHER PUBLICATIONS

McDonough, et al., Behavioral Correlates of Soman-Induced Neuropathology: Deficits in DRL Acquisition, Neurobehavioral Toxicology and Teratology, 1986, pp. 179-187, vol. 8.
U.S. Office Action dated Jun. 25, 2008 issued in U.S. Appl. No. 11/555,995, 23 pages.
U.S. Office Action dated Nov. 28, 2008 issued in U.S. Appl. No. 11/555,995, 8 pages.
International Search Report and Written Opinion of the ISA issued in PCT/US09/35539 dated Jul. 17, 2009 (8 pgs).
International Search Report and Written Opinion of the ISA issued in PCT/US09/52457 dated Oct. 6, 2009 (9 pgs).
Luo et al, "An In Vitro Comparative Study on the Reactivation of Nerve Agent-Inhibited Guinea Pig and Human Acetylcholinesterases by Oximes"; Biochemistry 2007, 46, pp. 11771-11779.
Garcia et al, "Sensitive and Rapid Blood and Tissue HPLC Oxime Assay and Pharmacokinetics of MMB-4 in Guinea Pigs and African Green Monkeys"; Walter Reed Army Institute of Research, Nov. 1, 2006, (8 pgs).
Chemistry and Industry; Applied Chemistry; Nigel Freestone; Nov. 7, 2005 (4 pgs).
Chemistry and Industry; New Drug Delivery Systems; Alexander T. Florence; Dec. 20, 1993 (7 pgs).
Advanstar Communications, Inc.; Pharmaceutical Technology; Vivek Kharb; Meenakshi Bhatia; Harish Dureja; Deepak Kaushik; Feb. 1, 2006 (11 pgs).
Advanstar Communications, Inc.; Pharmaceutical Technology Europe; Magdalene Radtke; Eliana B. Souto; Rainer H. Muller; Apr. 1, 2005 (4 pgs).
Dennison, et al. "Corticosteroids in rheumatoid arthritis," British Medical Journal vol. 316, pp. 789-790 (1998).
KENALOG® CREAMS Triamcinolone Acetonide Cream USPO. 025%, 0.1 %,0.5% (Online) http://dailymed.n1m.nih.gOY1dailymed/fda/fdaDrugXsl.cfm?id=1872&type=display; retrieved Jun. 21, 2008 (8 pages).
D. Farcasiu, et al. "Evaluation of hydrogen bonding by C-13NMR" Catalysis Letters 31 (1995) 351-358.
Praetorius, et al., "Engineered Nanoparticles in Cancer Therapy," Recent Patents on Drug Delivery & Formation 2007,vol. 1 No. 1, pp. 37-51.
Biosante Pharmaceuticals, "Hormone Therapy-A Multi-Billion Dollar Market," Investor Fact Sheet Sep. 2007; www.biosantepharma.com; (2 pages).
T.Welzel, et al., "Transfection of Cells With Custom-made Calcium Phosphate Nanoparticles Coated With DNA"; The Royal Society of Chemistry 2004; J. Mater. Chem. 2004, 14, pp. 2213-2217.
S. Bisht, et al., "pDNA Loaded Calcium Phosphate Nanoparticles: Highly Efficient Non-Viral Vector for Gene Delivery"; International Journal of Pharmaceutics 288 (2005), pp. 157-168.
T.Liu, et al., "Calcium Phosphate Nanoparticles As a Novel Nonviral Vector for Efficient Transfection of DNA in Cancer Gene Therapy"; Cancer Biotherapy & Radiopharmaceuticls, vol. 20, No. 2, 2005, pp. 141-150.
A. Brioschi, et al, "Solid Lipid Nanoparticles: Could They Help . . . "; Neurological Research 2007, vol. 29, Apr. 2007; pp. 324-330.
M. Nahar, et al, "Functional Polymeric Nanoparticles: An Efficient . . . "; Critical Reviews™ in Therapeutic Drug Carrier Systems, 23(4):259-318 (2006); Begell House Inc., http://begellhouse.com; downloaded Sep. 18, 2009 from IP 129.162.1.41 by Celia Frausto.
International Search Report and Written Opinion dated Nov. 23, 2009 issued in related International Patent Application No. PCT/US0959386.
U.S. Office Action dated Dec. 9, 2010 issued in related U.S. Appl. No. 11/555,995.
Giulian et al, "Short Communication", Optical and Quantum Electronics, vol. 9, pp. 263-264; 1977.
Patani et al, "Bioisosterism: A Rational Approach in Drug Design", (Chemical Reviews, vol. 96, No. 8, pp. 3147-3176; 1996.
U.S. Office Action dated Nov. 1, 2011 issued in related U.S. Appl. No. 11/555,995.
U.S. Office Action dated Aug. 15, 2011 issued in related U.S. Appl. No. 11/555,995.
European Supplementary Search Report—mailing date Sep. 27, 2011, issued in related European Appln. No. 09718843.7.
Sevelova et al, "Antidotal Treatment of GF-agent intoxication in mice with bispyridinium Oximes", Toxicology, vol. 207, No. 1, pp. 1-6, 2005.
Aurbek et al, "Analysis of Inhibition, Reactivation and Aging Kinetics of Highly Toxic Organophosphorus Compounds with Human and Pig Acetylcholinesterase", Toxicology, vol. 224, No. 1-2. pp. 91-99, 2006.
European Search Report dated Oct. 31, 2011 issued in related European Patent Application No. 09807064.2.
Office Action dated Nov. 29, 2011 issued in related U.S. Appl. No. 12/245,450.
Office Action dated Jan. 5, 2012 issued in related U.S. Appl. No. 12/702,095.
Office Action dated Jan. 26, 2012 issued in related U.S. Appl. No. 12/192,400.
Thiermann, "HI 6 dimethanesulfonate has better dissolution properties than HI 6 dichloride for application in dry/wet autoinjectors," International Journal of Pharmaceutics vol. 137, Issue 2, Jun. 28, 1996, pp. 167-176.
Bagryanskaya, et al., "Study of alkaloids from the flora of the Siberian and Altai regions. 6.* Crystal and molecular structure of songorine Z-oxime," Russian Chemical Bulletin, International Edition, vol. 50, No. 11, pp. 2092-2094, Nov. 2001.
Wu, et al., "Blood-Brain Barrier Transport of Reduced Folic Acid," Pharm Res. Mar. 1999;16(3):415-9.
Liu, et al., "Biologically active core/shell nanoparticles self-assembled from cholesterol-terminated PEG-TAT for drug delivery across the blood-brain barrier," Biomaterials 29 (2008) 1509-1517.
Hobbiger, et al., "Reactivation of Phosphorylated Acetocholinesterases by Pyridinium Aldoximes and Related Compounds," Biochem J. May 1960; 75(2): 363-372.
Kuca, et al., "Effective bisquaternary reactivators of tabun-inhibited AChE," J. Appl. ToxiCol. 2005; 25: 491-495.
Gao, et al., "Influence of particle size on transport of methotrexate across blood brain barrier by polysorbate 80-coated polybutylcyanoacrylate nanoparticles," International Journal of Pharmaceutics 310 (2006) 213-219.
Macauley, et al., Chromatographic separation and NMR characterization of the isomers of MMB-4 a bis-(pyridiniumaldoxime), Journal of Pharmaceutical and Biomedical Analysis 49 (2009) 889-894.
U.S. Office Action dated Mar. 11, 2011 issued in related U.S. Appl. No. 12/245,450.
U.S. Office Action dated May 25, 2011 issued in related U.S. Appl. No. 12/192,400.
Munavalli, et al; Preparation and Properties of Methylenebispyridinium Derivatives; Heterocycles 1986, vol. 24. No. 7; pp. 1883-1892.
Luo, et al., "Development of a broad-spectrum Oxime for the treatment of nerve agent toxicity," Conference paper, Division of Biochemistry, Walter Reed Army Institute of Research, Silver Spring, MD 20910, Report Date: Nov. 2006 Report No. A376184. Available at http://www.dtic.mil/cgi-bin/GetTRDoc?Location=U2&doc=GetTRDoc.pdf&AD=ADA481673, retrieved on Mar. 9, 2011.
Alyautdin, et al., "Drug delivery to brain by nanoparticles," (2003) eksperimental'naya i Klinicheskaya Farmakologiya, 66 (2), pp. 65-68. English language Abstract can be found on p. 68, final paragraph.
Office Action dated Sep. 27, 2012 issued in related U.S. Appl. No. 12/702,095.
Office Action dated Oct. 11, 2012 issued in related U.S. Appl. No. 12/192,400.
Chaumeil; "Micronization: A Method of Improving the Bioavailability of Poorly Soluble Drugs"; Methods and Findings in Experimental and Clinical Pharmacology, Apr. 1998, vol. 20 (3): pp. 211-215; Copyright 1998 Prous Science, CCC: 0379-0355/98.
Garner, et al; Comparison of the Absorption of Micronized (Daflon 500 mg) and Nonmicronized 14 C-Diosmin Tablets After Oral Administration to Healthy Volunteers by Accelerator Mass Spectrometry and Liquid Scintillation Counting; Journal of Pharmaceutical Sciences, vol. 91, No. 1, Jan. 2002, pp. 32-40.

Choi, et al; Amorphous Ultrafine Particle Preparation for Improvement of Bioavailability of Insoluble Drugs: Grinding Characteristics of Fine Grinding Mills; Elsevier, International Journal of Mineral Processing, vol. 74, Supplement 1, Dec. 2004, pp. S165-S172.

Gelperina, et al., "Drug delivery to the brain using surfactant-coated poly(lactide-co-glycolide) nanoparticles: Influence of the formulation parameters," European Journal of Pharmaceutics and Biopharmaceutics (2009) doi:10.1016/j.ejpb.2009.09.003.

Kurakhmaeva, et al, "Brain targeting of nerve growth factor using poly(butyl cyanoacrylate) nanoparticles," Journal of Drug Targeting, 2009; 17(8): 564-574.

Hekmatara, et al., "Efficient systemic therapy of rat glioblastoma by nanoparticle-bound doxorubicin is due to antiangiogenic effects," Clinical Neuropathology, vol. 28—No. 3/2009 (153-164).

Zensi, et al., "Albumin nanoparticles targeted with Apo E enter the CNS by transcytosis and are delivered to neurones," Journal of Controlled Release 137 (2009) 78-86.

Ulbrich, et al., "Transferrin- and transferrin-receptor-antibody-modified nanoparticles enable drug delivery across the blood-brain barrier (BBB)," European Journal of Pharmaceutics and Biopharmaceutics 71 (2009) 251-256.

Pereverzeva, et al., "Intravenous tolerance of a nanoparticle-based formulation of doxorubicin in healthy rats," Toxicology Letters 178 (2008) 9-19.

Kreuter, et al., "Use of nanoparticles for cerebral cancer," Tumori: 9-4: 271-277, 2008.

Kreuter, "Nanoparticles—a historical perspective," International Journal of Pharmaceutics 331 (2007) 1-10.

Petri, et al., "Mechanism of Action and Surfactant Influence During Chemotherapy of Brain Tumour Using Doxorubicin-Loaded Poly(butyl Cyanoacrylate) Nanoparticles," NSTI-Nanotech 2007, vol. 2, 2007, p. 386-389.

Ambruosi, et al., "Influence of surfactants, polymer and doxorubicin loading on the anti-tumour effect of poly(butyl cyanoacrylate) nanoparticles in a rat glioma model," Journal of Microencapsulation, Aug. 2006; 23(5): 582-592.

Ambruosi, et al., "Biodistribution of polysorbate 80-coated doxorubicin-loaded [14C]-poly(butyl cyanoacrylate) nanoparticles after intravenous administration to glioblastoma-bearing rats," Journal of Drug Testing, Feb. 2006; 14(2): 97-105.

Ambruosi, et al., "Body distribution of polysorbate-80 and doxorubicin-loaded [14C]-poly(butyl cyanoacrylate) nanoparticles after i.v. administration in rats," Journal of Drug Targeting, Dec. 2005; 13(10): 535-542.

Schuller et al., "Degradation of microvascular brain endothelial cell β-catenin after co-culture with activated neutrophils from patients undergoing cardiac surgery with prolonged cardiopulmonary bypass," Biochemical and Biophysical Research Communications 329 (2005) 616-623.

Kreuter, "Application of nanoparticles for the delivery of drugs to the brain," International Congress Series 1277 (2005) 85-94.

Kreuter, "Influence of the Surface Properties on Nanoparticle-Mediated Transport of Drugs to the Brain," Journal of Nanoscience and Nanotechnology, 2004, vol. 4, No. 5; p. 484-488.

Kreuter, "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles," Pharmaceutical Research, vol. 20, No. 3, Mar. 2003; p. 409-416.

Kreuter, "Transport of Drugs Across the Blood-Brain Barrier by Nanoparticles," Curr. Med. Chem.—Central Nervous System Agents, 2002, 2, 241-249.

Kreuter, et al."Apolipoprotein-medicated Transport of Nanoparticle-bound Drugs Across the Blood-Brain Barrier," Journal of Drug Testing, 2002 vol. 10 (4), pp. 317-325.

Gelperina, et al., "Toxicological studies of doxorubicin bound to polysorbate 80-coated poly(butyl cyanoacrykate) nanoparticles in healthy rats and rats with intracranial glioblastoma," Toxicology Letters 126 (2002) 131-141.

Kreuter, "Nanoparticulate systems for brain delivery of drugs," Advanced Drug Delivery Reviews 47 (2001) 65-81.

Ramge, et al., "Polysorbate-80 coating enhances uptake of polybutylcyanoacrylate (PBCA)-nanoparticles by human and bovine primary brain capillary endothelial cells," European Journal of Neuroscience, vol. 12, pp. 1931-1940 (2000).

Ramge, et al., "Circadian Phase-dependent Antinociceptive Reaction in Mice and the Tail-flick Test after Intravenous Injection of Dalargin-Loaded Nanoparticles," Chronobiology International, 16(6), 767-777 (1999).

Alyautdin, et al., "Drug delivery to brain by nanoparticles," (2003) eksperimental'naya i Klinicheskaya Farmakologiya, 66 (2), pp. 65-68.

Balali-Mood MD PHD, et al., "Neurotoxic Disorders of Organophosphorous Compounds and Their Managements," Arch Iranian Med 2008; 11 (1): 65-89.

Kuca, et al., "Preparation of Oxime HI-6 (Dichloride and Dimethanesulphonate)—Antidote against Nerve Agents," Defense Science Journal, vol. 58, No. 3, May 2008, pp. 399-404.

Antonijevic et al., "Unequal Efficacy of Pyridinium Oximes in Acute Organophosphate Poisoning," Clinical Medicine & Research, vol. 5, No. 1: 71-82, (2007).

Chambers, et al., "Development of a broad-spectrum Oxime for the treatment of nerve agent toxicity,", (Nov. 2006).

Kuca, et al., "In Vitro Reactivation Potency of Acetylcholinesterase Reactivators—K074 and K075—to Reactivate Tabun-inhibited Human Brain Cholinesterases," Neurotoxicity Research, 2007, vol. 11(2), pp. 101-106.

\* cited by examiner

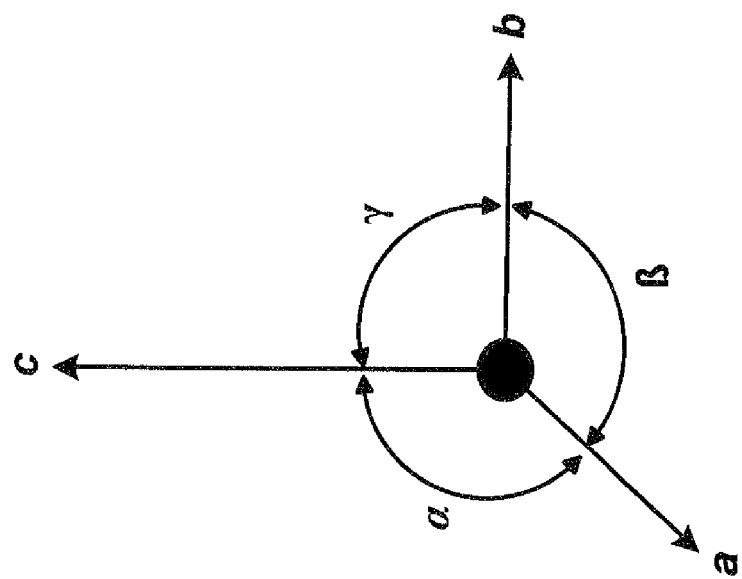
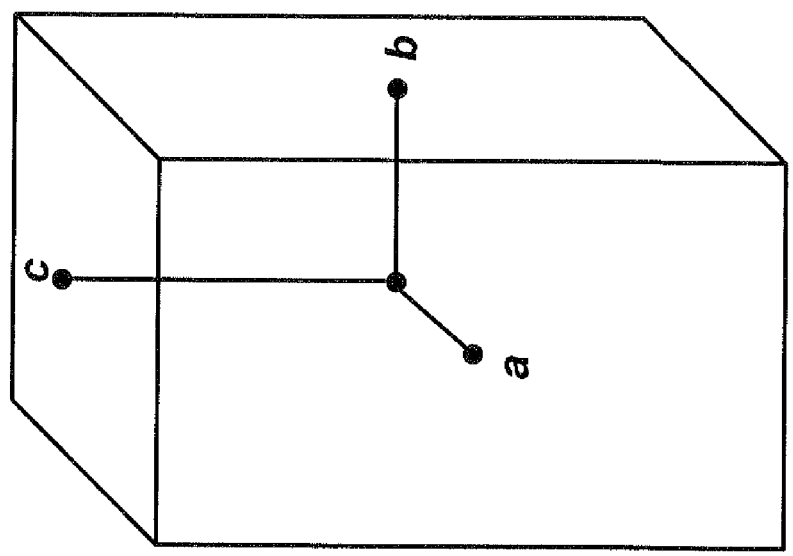
FIG. 6B

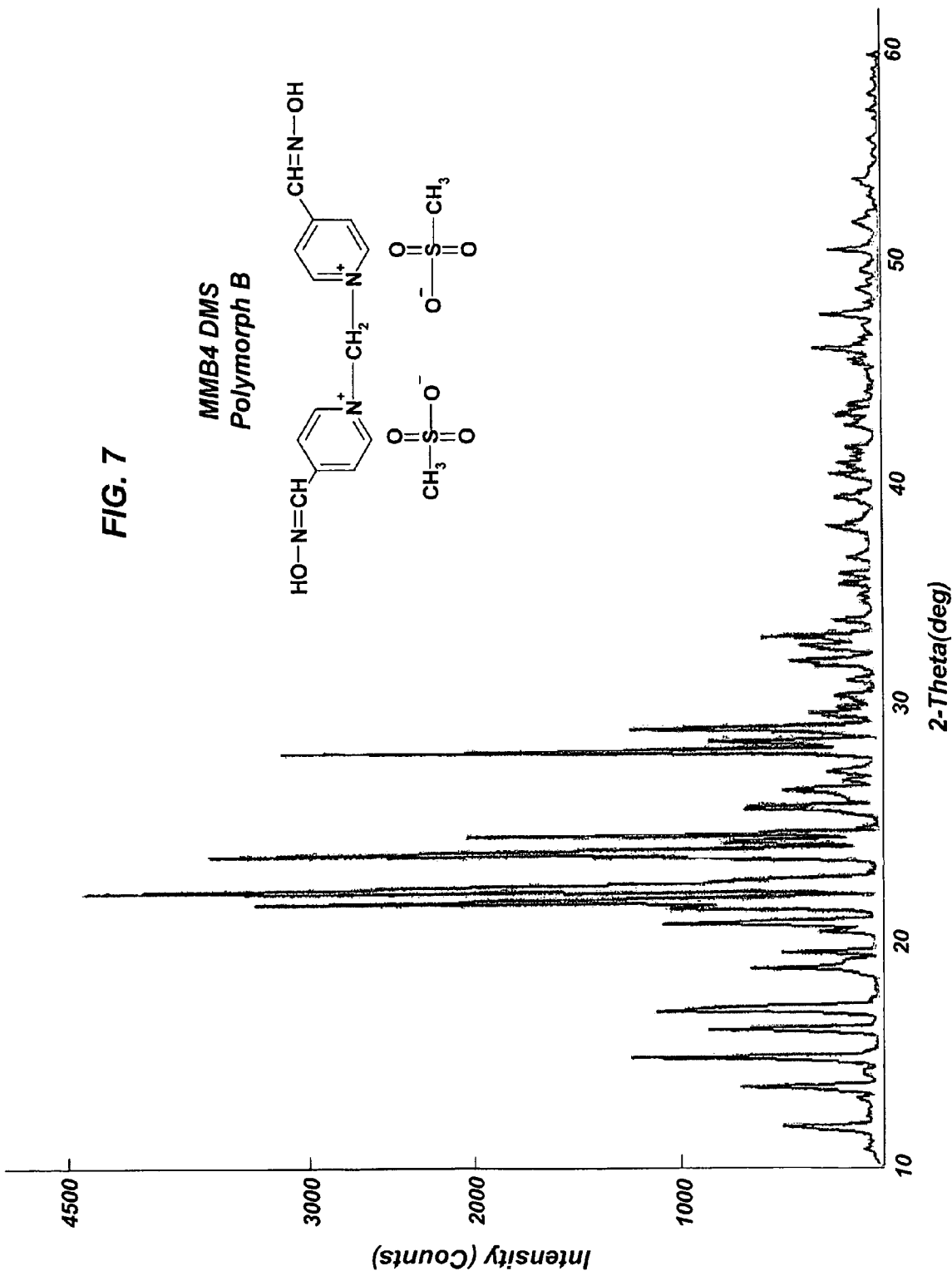

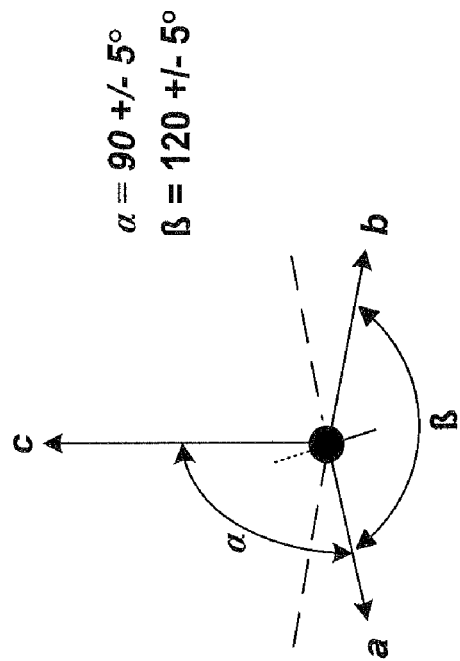
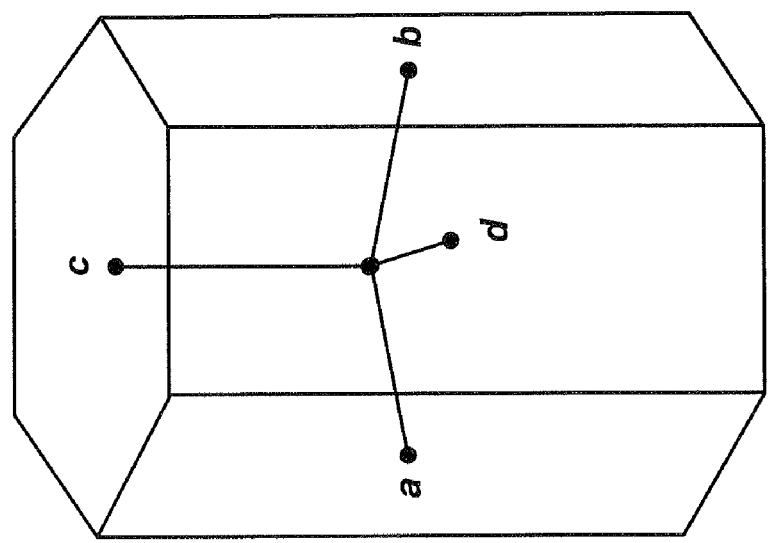
*FIG. 8B*

BIS-QUATERNARY PYRIDINIUM-ALDOXIME SALTS AND TREATMENT OF EXPOSURE TO CHOLINESTERASE INHIBITORS

GOVERNMENT RIGHTS CLAUSE

This invention was made with United States Government support under Contract No. W9113M-05-C-0199 awarded by the United States Army. The Government has certain rights in this invention.

FIELD OF THE INVENTION

The present invention relates to bis-quaternary pyridinium-aldoxime salts, their associated methods of preparation including their use for treatment of exposure to cholinesterase inhibitors, such as a phosphorous containing cholinesterase inhibitor type compounds.

BACKGROUND

Stimulating signals are typically carried by acetylcholine within a nervous system synapse. Such signals may be discontinued by a specific type of cholinesterase enzymes, acetylcholinesterase, which breaks down acetylcholine. If cholinesterase inhibiting chemicals are present, they may then prevent the breakdown of acetylcholine thereby disrupting normal nervous system activity. For example, certain chemical classes of pesticides, such as organophosphates and carbamates, may result in toxic cholinesterase inhibition. Accordingly, if an individual is regularly exposed to such inhibitors, there remains a need to prophylactically or therapeutically treat such toxicity. Among other things, individuals or animals who may have been exposed to a carbamate type cholinesterase inhibitor may currently be treated with atropine, and those exposed to organophosphates may beneficially be treated with a pralidoxime antidote.

SUMMARY

In a first exemplary embodiment, the present disclosure relates to a bis-quaternary pyridinium-2-aldoxime salt of the formula:

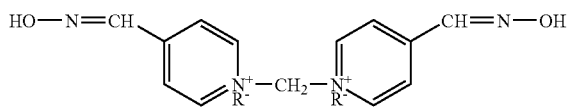

wherein R is a halogen and the salt indicates one or more distinguishing x-ray diffraction peaks at 2 Theta angles of 10-35 degrees as compared to non-distinguishing x-ray diffraction peaks at 2 Theta angles greater than 35 degrees.

In another exemplary embodiment, the present disclosure is directed at a bis-quaternary pyridinium-2-aldoxime salt of the formula:

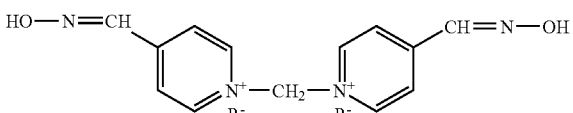

wherein R is a halogen and the salt indicates one or more distinguishing x-ray diffraction peaks at 2 Theta angles of 10-45 degrees as compared to non-distinguishing x-ray diffraction peaks at 2 Theta angles greater than 45 degrees.

In yet another exemplary embodiment, the present disclosure is directed at a bis-quaternary pyridinium-2-aldoxime salt of the formula:

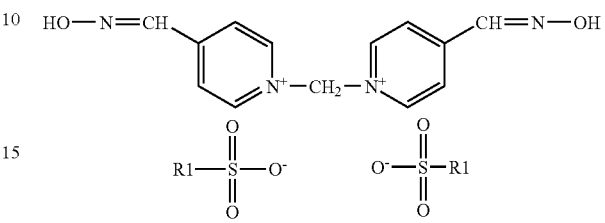

wherein R1 is a methyl and/or ethyl group and the salt indicates one or more distinguishing x-ray diffraction peaks at 2 Theta angles of 10-30 degrees as compared to non-distinguishing x-ray diffraction peaks at 2 Theta angles greater than 30 degrees and said salt has cubic rectangular crystal structure.

In another exemplary embodiment, the present disclosure is directed at a bis-quaternary pyridinium-2-aldoxime salt of the formula:

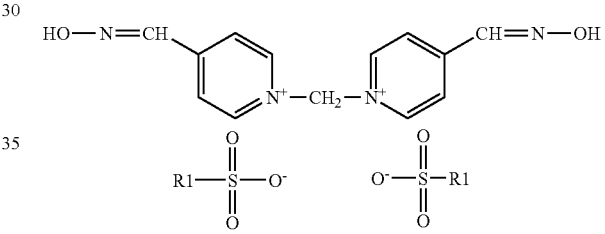

wherein R1 is a methyl and/or ethyl group and said salt indicates one or more distinguishing x-ray diffraction peaks at 2 Theta angles of 10-30 degrees as compared to non-distinguishing x-ray diffraction peaks at 2 Theta angles greater than 30 degrees and said salt has hexagonal crystal structure.

In yet another exemplary embodiment, the present disclosure is directed at a method for preparing a bis-quaternary pyridinium-2-aldoxime salt comprising supplying pyridine-4-aldoximine of the structure:

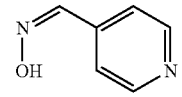

treating the pyridine-4-aldoximine with diodomethane to form 1,1'-methylenebis[4-[(hydroxyimino)methyl]-pyridinium]diodide of the following formula:

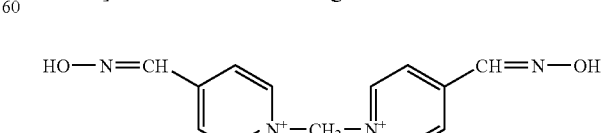

converting the 1,1'-methylenebis[4-[(hydroxyimino)methyl]-pyridinium]diodide to the following formula via ion exchange of the iodine to provide the following bis-quaternary pyridinium-2-aldoxime salt:

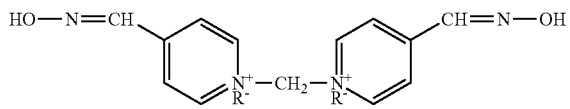

wherein R is a chlorine atom or an alkyl sulfonate group and where the alkyl sulfonate is of the general structure:

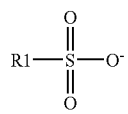

where R1 is a methyl or ethyl group.

In yet another exemplary embodiment, the present disclosure is directed at a prophylactic or therapeutic method of treating a person or animal for intoxication with a phosphorous containing cholinesterase inhibitor, comprising administering to a person or animal one or more of the following compounds:

(i) a bis-quaternary pyridinium-2-aldoxime salt of the formula:

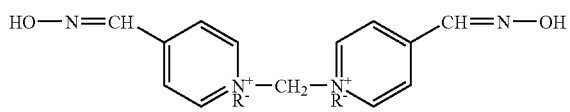

wherein R is a halogen and the salt indicates one or more distinguishing x-ray diffraction peaks at 2 Theta angles of 10-35 degrees as compared to non-distinguishing peaks at 2 Theta angles greater than 35 degrees; or (ii) a bis-quaternary pyridinium-2-aldoxime salt of the formula:

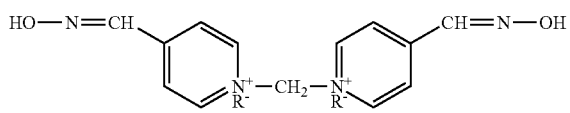

wherein R is a halogen and the salt indicates one or more distinguishing x-ray diffraction peaks at 2 Theta angles of 10-45 degrees as compared to non-distinguishing peaks at 2 Theta angles greater than 45 degrees; or (iii) a bis-quaternary pyridinium-2-aldoxime salt of the formula:

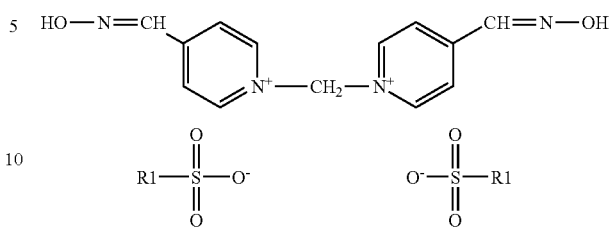

wherein R1 is a methyl and/or ethyl group and the salt indicates one or more distinguishing x-ray diffraction peaks at 2 Theta angles of 10-30 degrees as compared to non-distinguishing x-ray diffraction peaks at 2 Theta angles greater than 30 degrees and said salt has cubic rectangular crystal structure; or (iv) a bis-quaternary pyridinium-2-aldoxime salt of the formula:

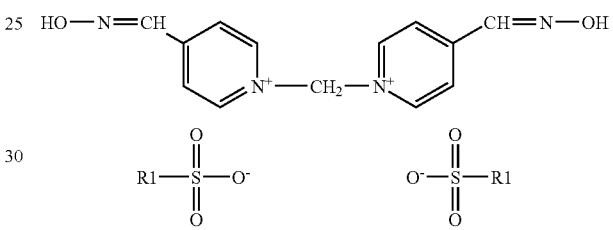

wherein R1 is a methyl and/or ethyl group and the salt indicates one or more distinguishing x-ray diffraction peaks at 2 Theta angles of 10-30 degrees as compared to non-distinguishing x-ray diffraction peaks at 2 Theta angles greater than 30 degrees and said salt has hexagonal crystal structure.

BRIEF DESCRIPTION OF THE DRAWINGS

FIG. 6B is an illustration of the crystalline structure of MMB4 DMS Polymorph A identified in FIG. 6A.
FIG. 7 is an X-ray diffraction pattern for MMB4 DMS Polymorph B.
FIG. 8B is an illustration of the crystalline structure of MMB4 DMS Polymorph B identified in FIG. 8A.

DETAILED DESCRIPTION

Figure 1:
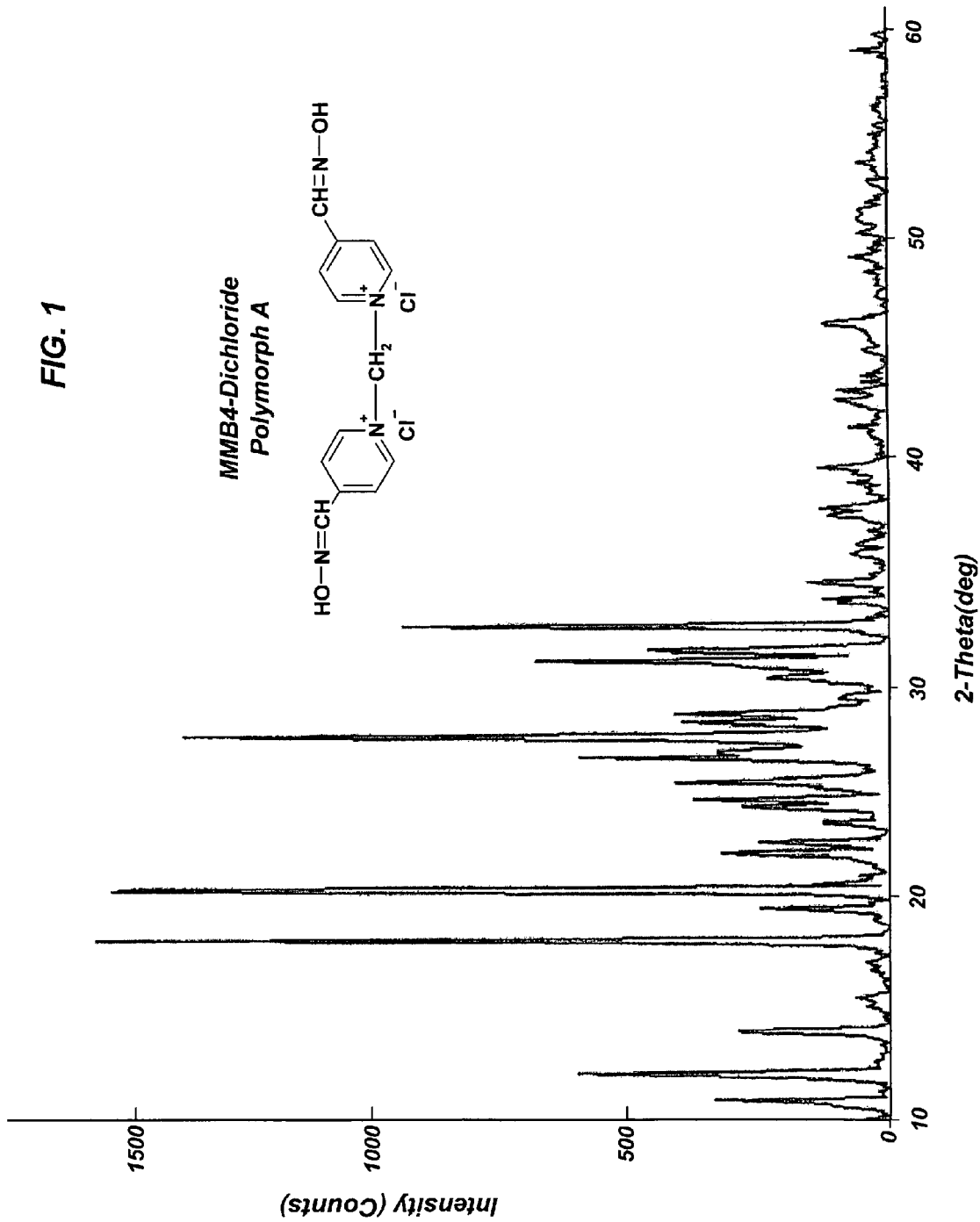
FIG. 1 is an X-ray diffraction pattern for MMB4-Dichloride Polymorph A.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

As alluded to above, the present disclosure is directed at the formation of certain bis-quaternary pyridinium aldoxime salts and their associated use to prophylactically and/or therapeutically treat intoxication in a person or animal due to the presence of a cholinesterase inhibitor, such as a phosphorous containing cholinesterase inhibitor. It is therefore worth pointing out that organophosphates (OPs) may act as hemi-substrates of cholinesterase by specifically phosphorylating the active site serine. As the rate of hydrolysis of the phosphoryl or phosphonyl enzyme may be relatively slower than deacylation of acetylcholine, OPs are effectively irreversible cholinesterase inhibitors. OPs have also been developed as chemical weapon systems, and relatively potent insecticides, due to their inhibition of the insects' flight muscle cholinesterase, with resulting paralysis and death. It may therefore be appreciated that intoxication by anti-cholinesterase compounds may develop following accidental exposure to organophosphorus insecticides and/or other associated chemical agents. Furthermore, the overall pharmacologic effect of anti-cholinesterases may be due to the inhibition of cholinesterase enzymes throughout the body.

In a first exemplary embodiment, the present disclosure relates to the preparation of a 1,1'-methylenebis[4-(hydroxyimino)methyl]-pyridinium salt, which may be represented by the following general formula:

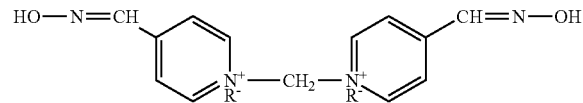

where R may be a halide counteranion such as a halogen (e.g. Cl⁻ or Br⁻ or I⁻) in which case the compound may be referred to as "MMB4 Dihalide.". More generally, R may be derived from a salt of an inorganic or organic acid. For example, the anion may be derived from hydrogen sulfate ($H_2SO_4$), nitrate, fumarate, lactate, tartate, citrate, and/or acetate.

In addition, R may be a counteranion such as an alkyl sulfonate group. In such a case, the 1,1'-methylenebis[4-(hydroxyimino)methyl]-pyridinium salt would assume the following general formula:

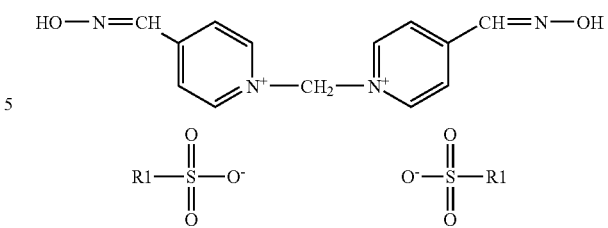

wherein R1 may be selected such that it does not interfere (e.g. steric interference) with the formation of the particular polymorphic pyridinium salts noted below. Accordingly, R1 may be a methyl (—$CH_3$) group, and it is contemplated herein that it may also include ethyl type group functionality (—$CH_2CH_3$).

One particularly useful and convenient synthetic procedure for the formation of the pyridinium salts of the present disclosure may involve the preparation of 1,1'-methylenebis[4-[(hydroxyimino)methyl]-pyridinium]diodide hereinafter referred to as "MMB4 DI", which may then be converted to 1,1'-methylenebis[4-[(hydroxyimino)methyl]-pyridinium] dimethanesulfonate "MMB4 DMS." This synthetic procedure is outlined in the general reaction scheme illustrated below:

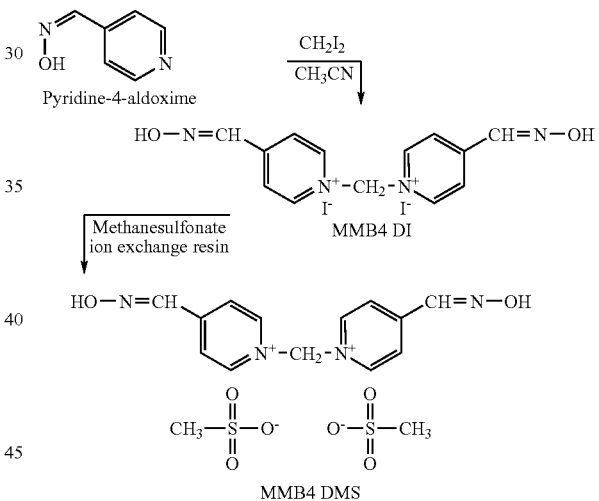

In addition, it may be appreciated that the MMB4 DI may be converted, again by the convenient procedure of ion exchange, to a particular dihalide salt, such as the dichloride salt, as illustrated below:

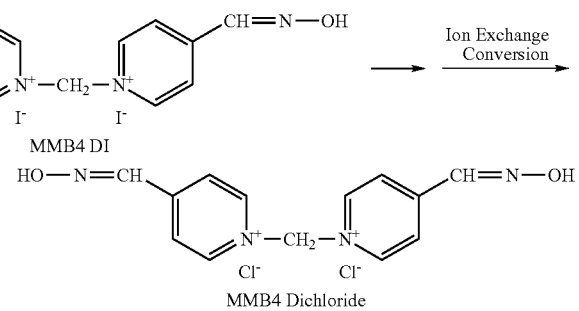

It has been determined that the MMB4 dichloride and/or the MMB4 DMS compounds noted above may be isolated in one of two polymorphic forms, as disclosed herein, by control of, e.g., the solvents that may be employed for the pyridinium salt recrystallization. In addition, such polymorphic forms, as also noted above, provided the ability to offer improved prophylactic or therapeutic treatment of a person or animal intoxicated with a cholinesterase inhibitor. Accordingly, attention is therefore next directed to FIG. 1, which provides the x-ray diffraction pattern [intensity (counts) versus 2-Theta(degrees)] for the MMB4 dichloride compound in the form of what may now be termed MMB4-dichloride Polymorph A. The diffraction patterns (as well as the other diffraction patterns reported herein) were made on a Siemens Kristalloflex 805 with a model D500 goniometer, serial number WM80030464X. The diffraction patterns were then processed using JADE v3.1 from Materials Data, Inc (program serial number MDI-R95704. In general, a representative portion of the sample for analysis was ground to a grain size of less than 25 microns and then spread on a polycarbonate specimen holder. The x-ray tube was run at 40 kV and 30 mA with a 2-theta range of 10-60 degrees. The instrument may be calibrated at regular intervals using appropriate standards.

As can be seen from FIG. 1, the MMB4 dichloride compound in the form of polymorph A herein indicates one or more x-ray diffraction peaks with relative intensity counts (artificial units) between 500-1500 at the 2 Theta angles of between 10-35 degrees, which relatively intensity counts for the peaks drop to a level of less than 500 counts at 2 Theta angles of greater than about 35 degrees. That is, no peaks are present with relative intensity counts of more than 250 at 2 Theta angles between 35-60 degrees. Accordingly, it may be understood herein that the MMB4 dichloride compound in the form of polymorph A may be characterized as having an x-ray diffraction pattern with distinguishing peaks at the 2 Theta angles of between 10-35 degrees as compared to the non-distinguishing x-ray diffraction peaks at the 2 Theta angles of greater than 35 degrees. By reference to distinguishing peaks, it may be understood (upon consideration of FIG. 1) as those peaks and/or collection of peaks within the 2 Theta angles of 10-35 degrees which then may be employed to provide identifiable d-spacing (Braggs Law) for the MMB4 dichloride polymorph A. Accordingly, reference to a collection of peaks herein may include, e.g. information sourced from 2-100 peaks, including all values and increments within the range of 2-100.

Figure 2:
FIG. 2 is a scanning electron micrograph of MMB4 Dichloride Polymorph A.

Attention is therefore next directed to FIG. 2, which provides a scanning electron micrograph of MMB4 dichloride Polymorph A. As can be seen, MMB4 dichloride Polymorph A may also be characterized as having a needle-like particulate structure, with an aspect ratio (AR) or length divided by largest diameter of greater than 2:1. More particularly, the aspect ratio may be in the range of 2:1 to 16:1, including all values and increments therein.

Figure 3:
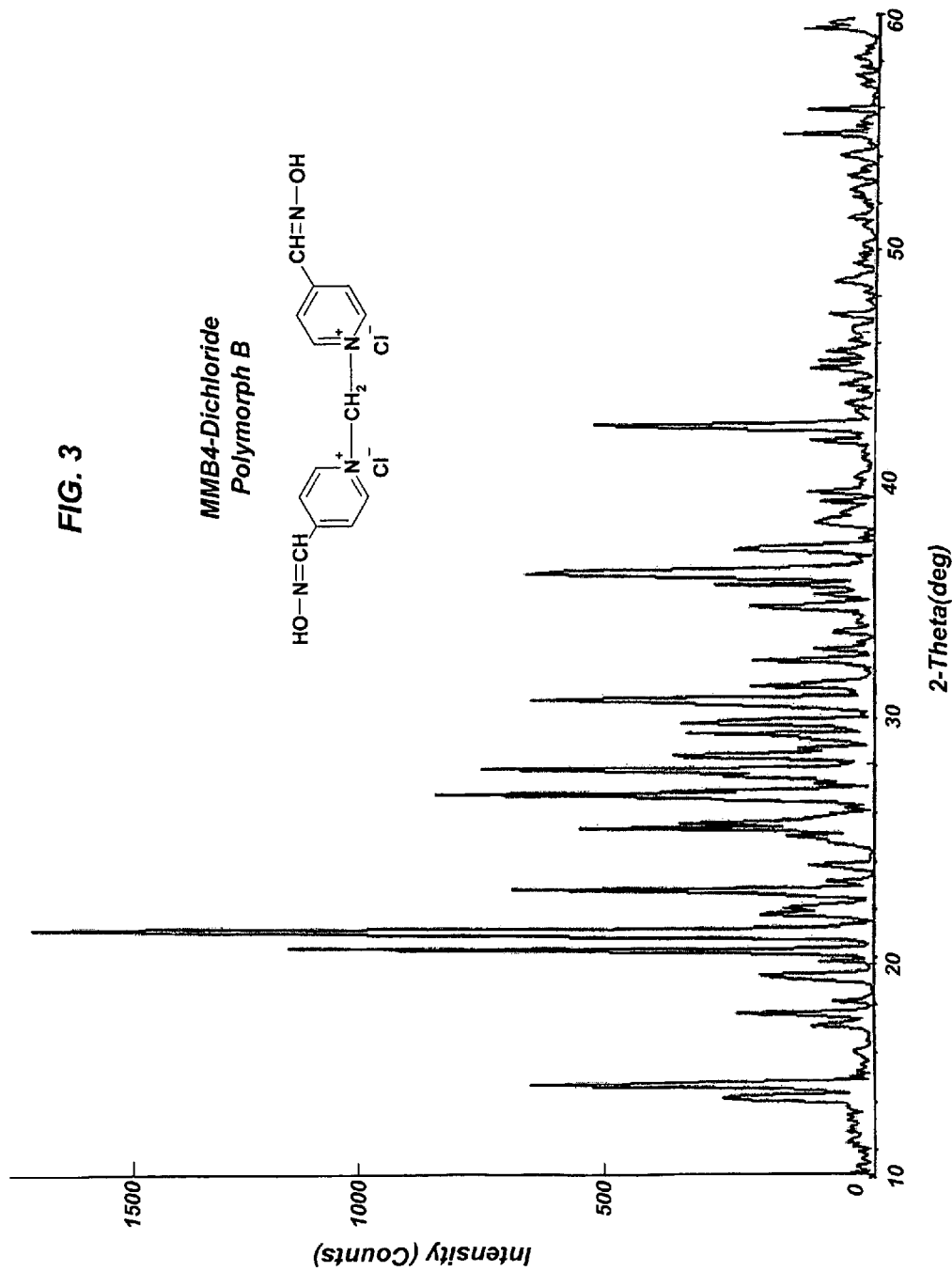
FIG. 3 is an X-ray diffraction pattern for MMB4 Dichloride Polymorph B.

Attention is next directed to FIG. 3, which provides the x-ray diffraction pattern of MMB4 dichloride Polymorph B. As can be seen, MMB4 dichloride Polymorph B indicates one or more x-ray diffraction peaks having relative intensity counts (artificial units) between 500-1500 at the 2 Theta angles of between 10-45 degrees, which relatively intensity counts for the peaks drop to a level of less than 500 counts at 2 Theta angles greater than about 45 degrees. That is, no peaks are present with relative intensity counts of more than 250 at 2 Theta angles between 45-60 degrees. Accordingly, it may be understood herein that the MMB4 dichloride compound in the form of polymorph B may be characterized as having an x-ray diffraction pattern with distinguishing peaks at the 2 Theta angles of between 10-45 degrees as compared to the non-distinguishing x-ray diffraction peaks at the 2 Theta angles of greater than 45 degrees. By reference to distinguishing peaks, it may again be understood (upon consideration of FIG. 3) as those peaks and/or collection of peaks within the 2 Theta angles of 10-45 degrees which then may be employed to provide identifiable d-spacing (Braggs Law) for the MMB4 dichloride polymorph B.

Figure 4:
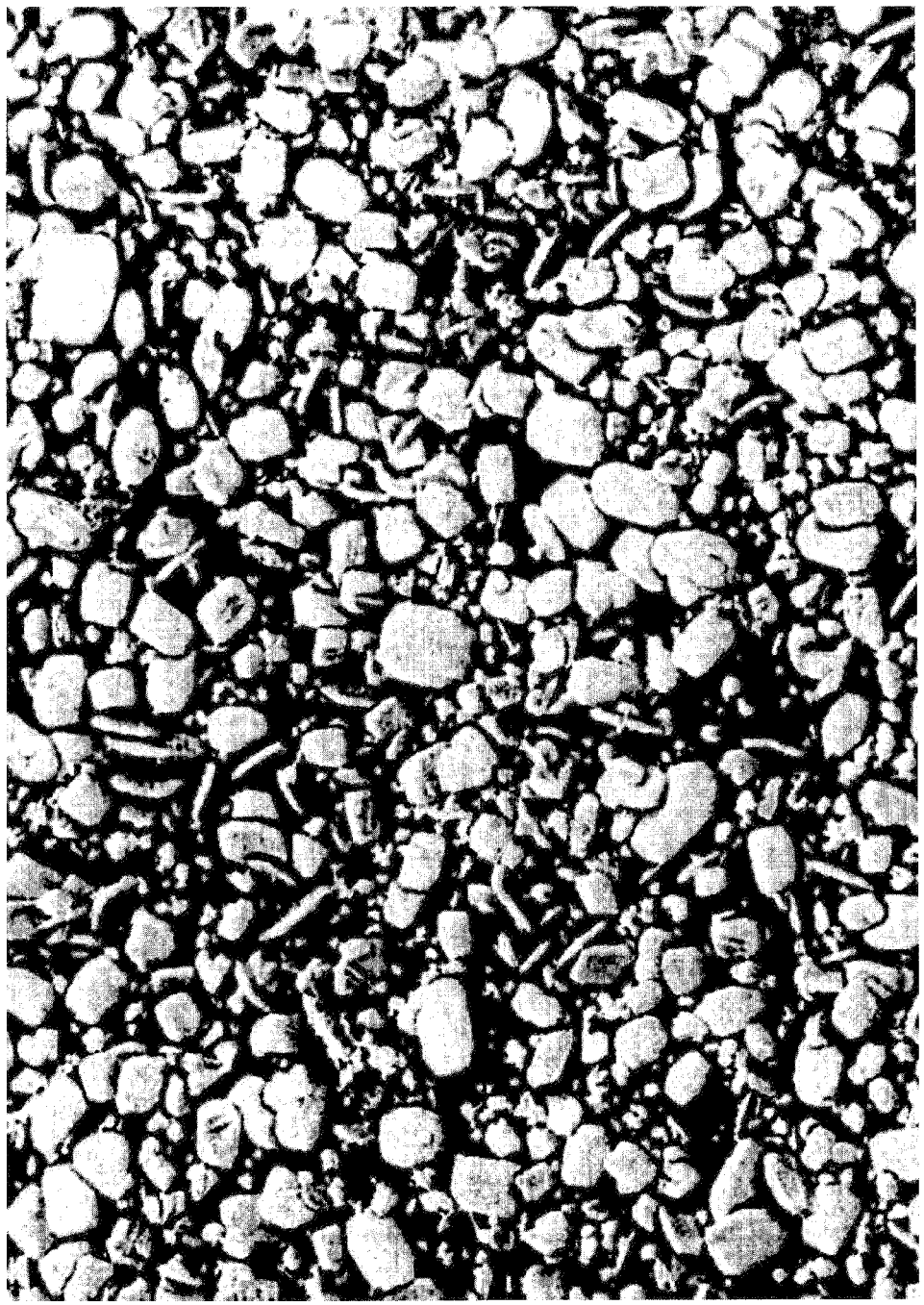
FIG. 4 is a scanning electron micrograph of MMB4 Dichloride Polymorph B/

Attention is therefore next directed to FIG. 4 which provides a scanning electron micrograph of MMB4 dichloride Polymorph B. As can be seen, MMB4 dichloride Polymorph B may also be characterized as having either a particulate structure that is of a square, rectangular, rhomboid (i.e. a parallelogram in which adjacent sides are of unequal lengths) and/or rhombus (a rhomboid with right angled corners) type geometry.

Figure 5:
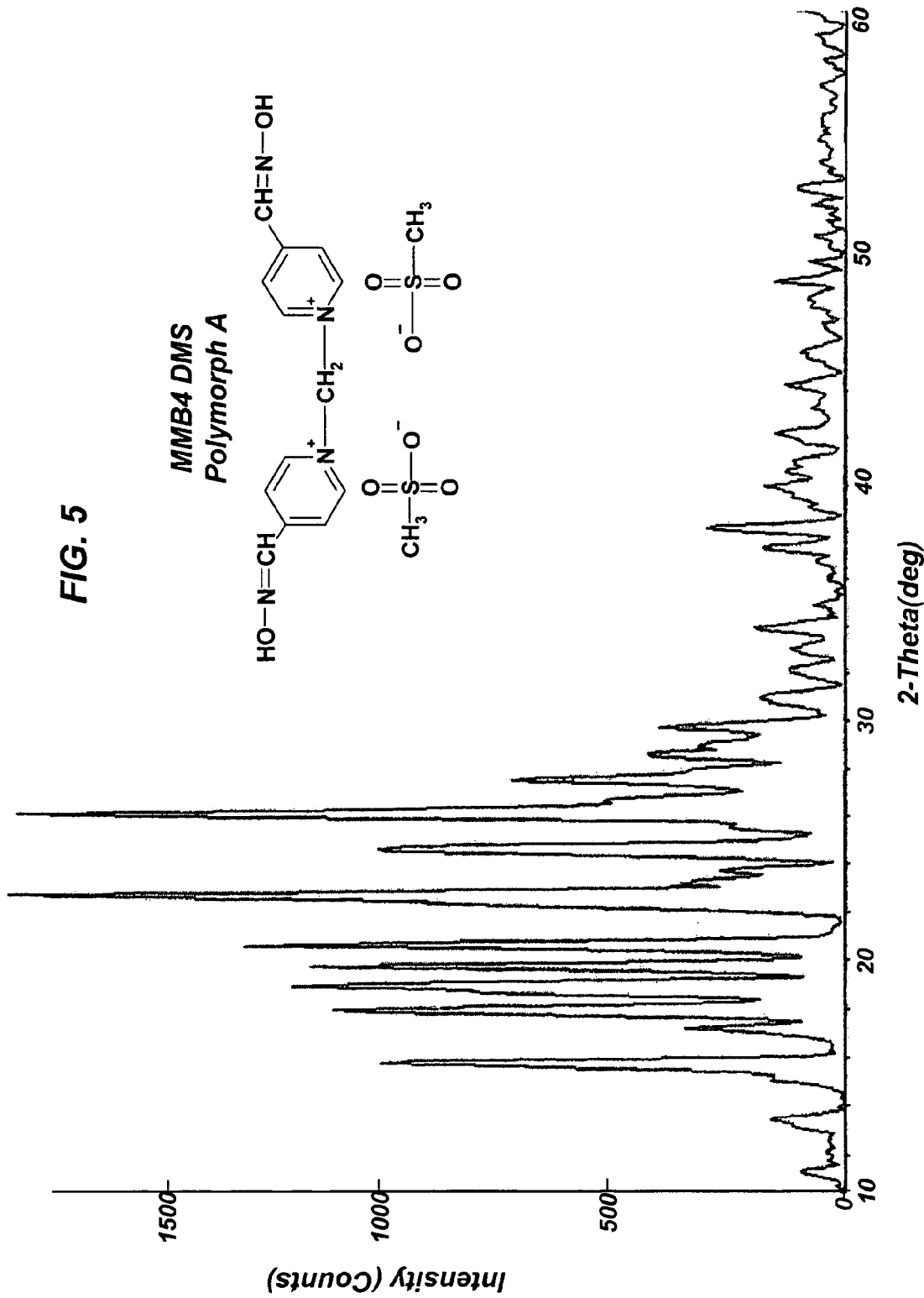
FIG. 5 is an X-ray diffraction pattern for MMB4 DMS Polymorph A.

Attention is next directed to FIG. 5 which provides the x-ray diffraction pattern of MMB4 DMS Polymorph A. As can be seen, MMB4 DMS Polymorph A indicates one or more x-ray diffraction peaks with relative intensity counts (artificial units) between 500-1500 at the 2 Theta angles of between 10-30 degrees, which relatively intensity counts for the peaks drop to a level of less than 500 counts at 2 Theta angles greater than about 30 degrees. That is, no peaks are present with relative intensity counts of more than 250 at 2 Theta angles between 30-60 degrees. Accordingly, it may be understood herein that the MMB4 DMS compound in the form of Polymorph A may be characterized as having an x-ray diffraction pattern with distinguishing peaks at the 2 Theta angles of between 10-30 degrees as compared to the non-distinguishing x-ray peaks at the 2 Theta angles in the range of greater than 30 degrees, e.g. in the range of greater than 30 degrees to about 60 degrees. By reference to distinguishing peaks, it may again be understood (upon consideration of FIG. 5) as those peaks and/or collection of peaks within the 2 Theta angles of 10-30 degrees which then may be employed to provide identifiable d-spacing (Braggs Law) for the MMB4 DMS Polymorph A.

Figure 6A:
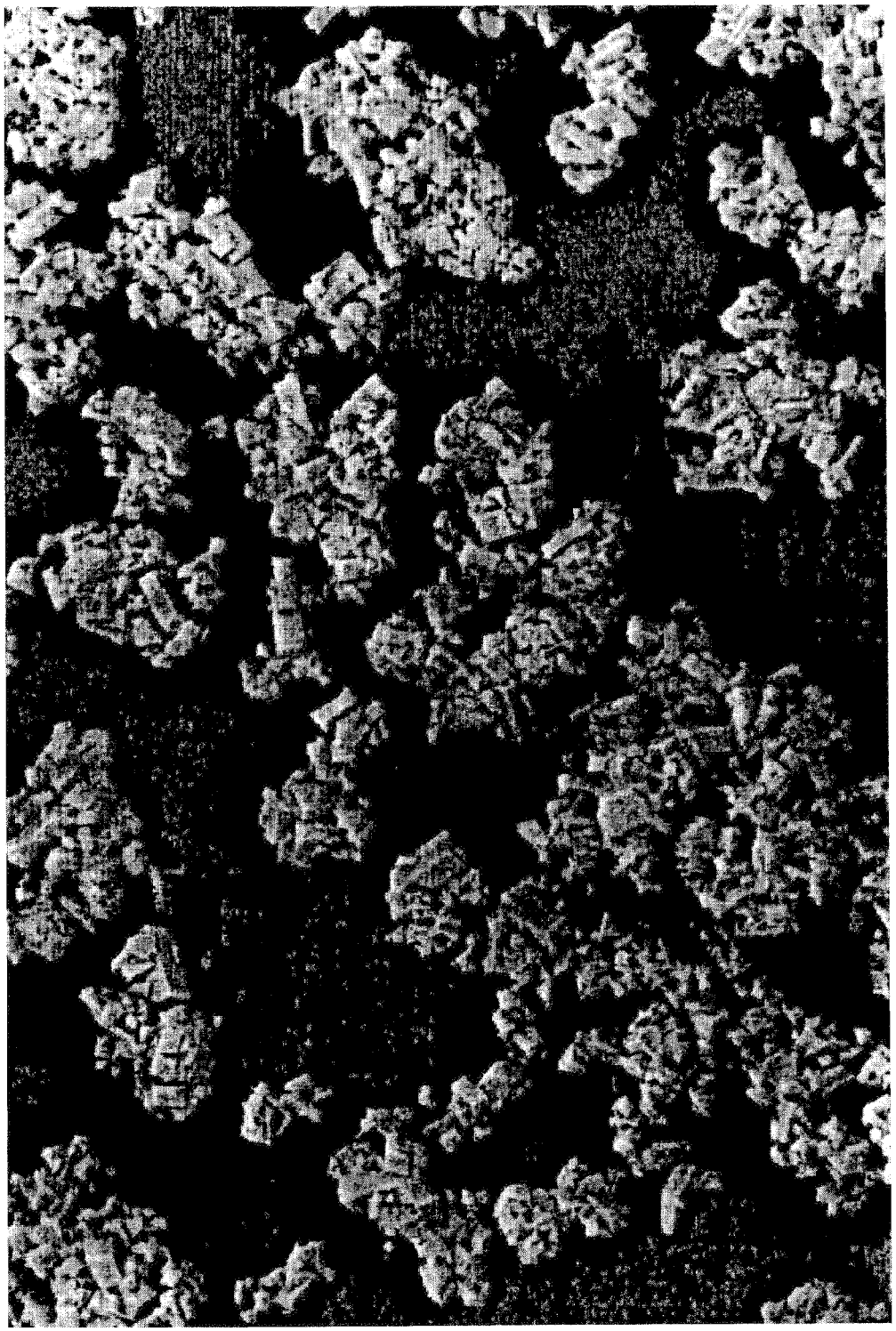
FIG. 6A is a scanning electron micrograph of MMB4 DMS Polymorph A.

FIG. 6A next provides a scanning electron micrograph of MMB4 DMS Polymorph A. As can be seen, MMB4 DMS Polymorph A may be described as having cubic rectangular type crystal structure or geometry. A cubic rectangular geometry may be understood as a cubic configuration that may be stretched along its (c) axis to provide a rectangular configuration, consisting of three substantially equal or equatorial (a, b and c) axes at 90° (+/−5°) and the c axis is longer than the horizontal axis. See FIG. 6B and angles α, β, and γ which are at 90° (+/−5°).

Attention is next directed to FIG. 7 which provides the x-ray diffraction pattern of MMB4 DMS polymorph B. As can be seen, MMB4 DMS Polymorph B indicates one or more x-ray diffraction peaks with relative intensity counts (artificial units) between 1000-4500 at the 2 Theta angles of between 10-30 degrees, which relatively intensity counts for the peaks drop to a level of less than 500 counts at 2 Theta angles greater than about 30 degrees. That is, no peaks are present with relative intensity counts of more than 500 at 2 Theta angles between 30-60 degrees. Accordingly, it may be understood herein that the MMB4 DMS compound in the form of polymorph B may be characterized as having an x-ray diffraction pattern with distinguishing peaks at the 2 Theta angles of between 10-30 degrees as compared to the non-distinguishing x-ray diffraction peaks at the 2 Theta angles of greater than 30 degrees. By reference to distinguishing peaks, it may again be understood (upon consideration of FIG. 7) as those peaks and/or collection of peaks within the 2 Theta angles of 10-30 degrees which then may be employed to provide identifiable d-spacing (Braggs Law) for the MMB4 DMS polymorph B.

Figure 8A:
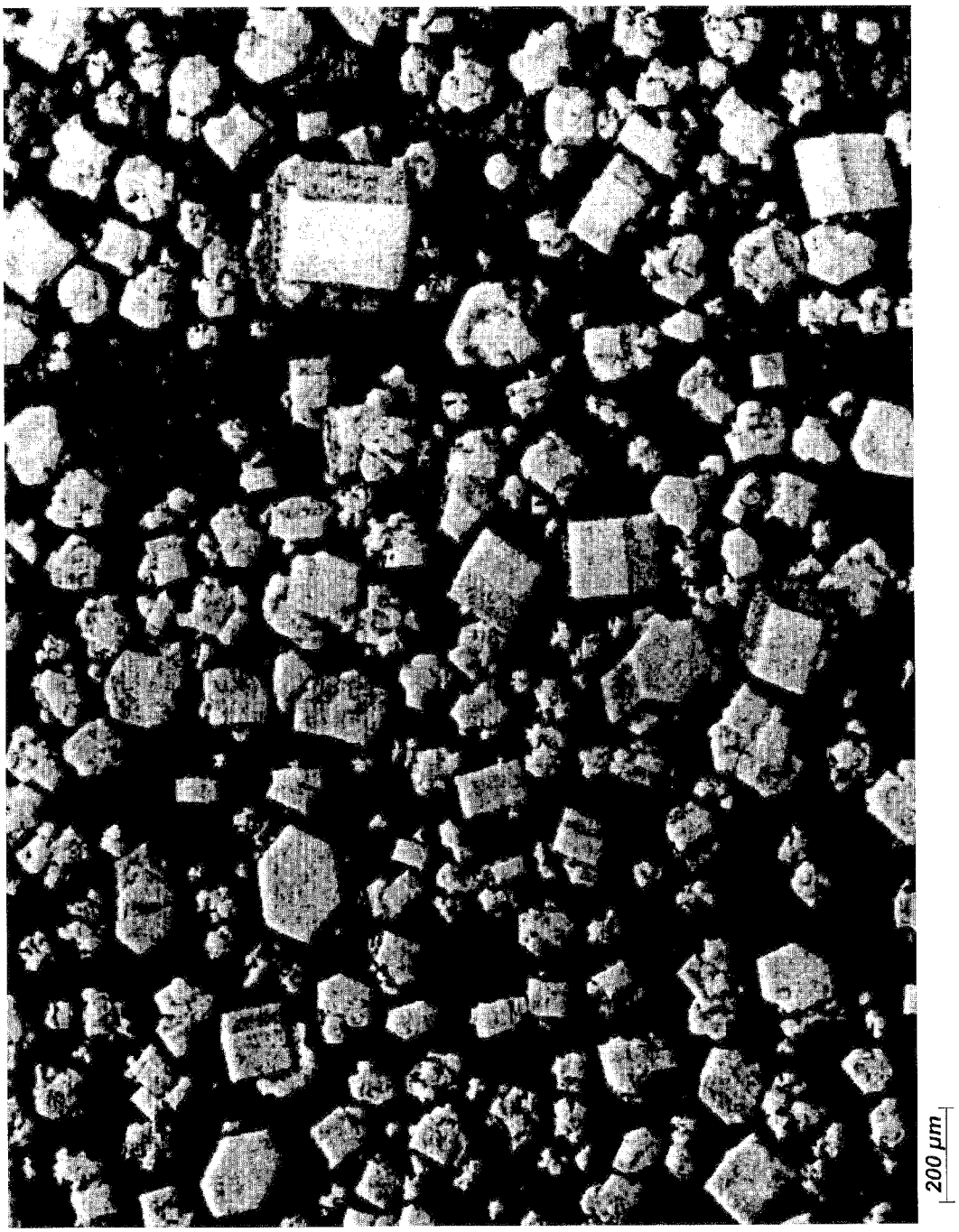
FIG. 8A is a scanning electron micrograph of MMB4 DMS Polymorph B.

FIG. 8A next provides a scanning electron micrograph of MMB4 DMS Polymorph B. As can be seen, MMB4 DMS Polymorph B may be described as having primarily hexagonal structure. A hexagonal crystal structure may be understood as having four crystallographic axes consisting of three substantially equal or equatorial (a, b, and d) axes at 120° (+/−5°) and one vertical (c) axis that is 90° (+/−5°) to the other three. See, e.g., FIG. 8B, wherein angle α is shown being equal to 120° (+/−5°) and angle β being equal to 90° (+/−5°). The (c) axis may be shorter or longer than the horizontal axis.

Once prepared, the 1,1'-methylenebis-quaternary pyridinium-4-aldoximine compounds, either in the form of polymorph A and/or polymorph B, may be readily incorporated into a pharmaceutically acceptable carrier. As noted, such compounds may then be administered in an antidotal amount to therapeutically treat exposure to a phosphorous containing cholesterase inhibitor. A pharmaceutically acceptable carrier may therefore be understood herein as an aqueous formulation containing the above 1,1'-methylenebis-quaternary pyridinium-4-aldoximine salt compounds in the form of what has been identified herein as polymorph A and/or polymorph B. Such formulations may therefore amount to aqueous solutions, suspensions and/or emulsions and may be adjusted to have a pH of 1.0 to 5.0, including all values and increments therein. Furthermore, it may be appreciated that an emulsion may be understood as an aqueous mixture containing the subject compound in the presence of suitable hydrophobic/hydrophilic emulsifying agents.

The pharmaceutically acceptable carrier may also provide a pharmaceutically acceptable anion, which as noted above, may be sourced from an inorganic or organic acid, which acids may or may not include a preservative. Accordingly, the 1,1'-methylenebis-quaternary pyridinium-4-aldoximine salt compounds, either in the form of polymorph A and/or polymorph B may be present herein in the aqueous formulation at a concentration of 0.1-50% by weight, including all values and increments therein. It may be appreciated, however, that the specific doses may depend on a variety of factors, for example, the age, body weight, general state of health and time of administration and the time and severity of exposure. It is worth noting that parenteral administration may be utilized herein, whether for prophylaxis or therapeutically (i.e., before exposure to a cholinesterase inhibitor).

In addition, the pharmaceutically acceptable aqueous carrier herein may include other diluents suitable for preparing oral pharmaceutical suspension. For example, an oral pharmaceutical suspension of the present invention may include, if necessary, pharmaceutically acceptable additives including auxiliary substances, stabilizing agents, suspending agents, surface tension modifiers, viscosity modifiers, colorants, preservatives, flavoring agents and other commonly used additives such as lactose, citric acid, tartaric acid, stearic acid, magnesium stearate, sucrose, and the like.

The present disclosure may therefore now be considered with respect to the following various non-limiting examples.

EXAMPLE 1

Preparation of MMB4 Dimethane Sulfonate
(Laboratory Scale)

(1) Production of MMB4 Diiodide

To 21.53 g (0.176 mol) of pyridine-4-aldoxime in 250 mL of acetonitrile was added 27.21 g (0.176 mol) of diiodomethane. The reaction mixture was refluxed under argon for 90 hours. The mixture was cooled, filtered and the filter cake washed with 100 ml of acetonitrile. The filter cake was air dried for 30 minutes to yield 41.52 g. The cake was dried under high vacuum to give 41.02 g (91% yield).

(2) Dimethanesulfonate Resin Preparation

In a 250 mL beaker, 30 g of Dowex 550A (OH form), available from the Dow Chemical Company, was added to 84 mL of 10% (v/v) methanesulfonic acid in methanol. The resin was stirred at room temperature for 2 h then filtered through a 150 mL sintered funnel. The resin bed was washed with 2×84 mL portions of methanol and then air-dried for 30 minutes. Total resin weight: 17.6 g, divided into 2×8.8 g portions.

(3) Conversion of MMB4 Diiodide to MMB4 Dimethanesulfonate

A sample of 2.0 g (3.9 mmol) of MMB4 diiodide was dissolved in 100 mL of methanol with stirring in a 50° C. water bath. The solution was cooled to room temperature, then 8.8 g of the mesylate form of Dowex 550A was added and stirred at room temperature for 2 hours. The mixture was filtered through a sintered funnel, washing the resin bed with 10 mL of methanol. An additional 8.8 g of the mesylate form of Dowex 550A was added to the filtrate and the mixture stirred for an additional 2 h. The mixture was filtered and the resin bed washed with 10 mL of methanol.

The filtrate was concentrated to 10 mL, then 35 mL of denatured ethanol (denatured with 5% isopropanol and 5% methanol) was added. The mixture was heated to 50° C. with stirring until complete dissolution (30 min). The solution was allowed to stand for 16 hours at ambient temperature with slow stirring. The mother liquor was decanted and the solids rinsed with 2×5 mL of cold (5° C.) denatured ethanol. The solid was dried at 23 mm Hg and room temperature to yield 1.35 g (77%) of a tan-amber solid (Polymorph A).

EXAMPLE 2

Preparation of MMB4 Dimethanesulfonate
(Production Scale)

(1) Production of MMB4 Diiodide

A 100-gallon (380 L) reactor is charged with 21.9 kg (179 moles) of pyridine-4-aldoxime and 170 kg of acetonitrile, followed by 48.3 kg (180 moles) of diiodomethane and 37.5 kg of acetonitrile. The mixture is brought to a gentle reflux (approximately 84° C.) with vigorous mechanical stirring under an inert atmosphere (nitrogen). After 72 hours, the mixture is cooled to 40-45° C. with stirring over 5 hours. The resulting suspension is filtered and then washed three times with 25 kg portions of 40-45° C. acetonitrile. The washed filter cake is transferred to drying trays and dried under vacuum with heating 40-45° C. over eight hours. This process yields approximately 37.5 kg (82%) of MMB4 diiodide.

(2) Dimethanesulfonate Resin Preparation

In a 100-gallon (380 L) reactor, 172 kg of methanol is slowly charged to methanesulfonic acid (35.7 kg), maintaining the temperature at 20-40° C. This solution is subsequently added to 77.5 kg of Dowex 550A (OH form), maintaining the temperature below 50° C. The resultant resin/methanol/methanesulfonic acid slurry is then stirred at 25±5° C. for 2-2.5 hours and then filtered. The resin is washed in a plug flow manner with two-153 kg portions of methanol. A final wash of 35 kg of methanol is used to test for residual water; the in-process limit is no more than 0.4%.

(3) Conversion of MMB4 Diiodide to MMB4 Dimethanesulfonate

In a 100-gallon (380 L) reactor, MMB4 diiodide, 10.3 kg, is dissolved in 204.5 kg of methanol with stirring by warming to 50±3° C. for 1-1.5 hours. While maintaining the temperature, half of the previously formed dimethanesulfonate resin is added and stirred at 50±3° C. for 2 to 2.5 hours. The solution is then filtered and the resin is washed with 20.5 kg of methanol. The filtrate and wash are combined and treated as described above with the remaining half of the resin.

After the final filtration and washing, an in-process test is used to monitor iodide concentration. The wash and filtrate are combined and then reduced to a volume of 65-70 L under vacuum at a temperature less than 25° C. After concentrating, 5.5 kg each of isopropanol and methanol are added followed by 98 kg of ethanol. The mixture is heated to reflux (approximately 72° C.) for 1-1.5 hour to achieve complete dissolution.

Once clarity is achieved, the mixture is allowed to cool to 20±5° C. over approximately 9 hours to crystallize, followed by an additional hold time of 7-7.5 hours. The MMB4 dimesylate is then filtered and washed with a mixture of 4.5 kg ethanol and 2.3 kg of methanol. The filter cake is then dried at ambient temperature under vacuum for 8 hours. The typical yield is 5-5.7 kg or 55-63% of MMB4 dimethanesulfonate (Polymorph B).

EXAMPLE 3

A representative pharmaceutical formulation for MMB4 DMS is set forth below:

450 mg/mL of MMB4 DMS and 5 mg/mL of benzyl alcohol in WFI is adjusted with an acetic acid solution to a pH of about 2.3. The following were then transferred to a 5 mL volumetric flask: 25 mg benzyl alcohol (BA), 1.0 g "0.3% Acetic acid solution" and 2.25 g MMB4 DMS. At this point, WFI water is added to dissolve the solids completely. The pH is then measured and adjusted with acetic acid solution to a pH of about 2.3. At this point one brings the total volume to 5 mL with WFI water. This is then followed by filtering through a 0.2-micron syringe filter.

What is claimed is:

1. A bis-quaternary pyridinium-2-aldoxime salt of the formula:

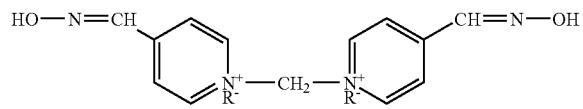

wherein R is a halogen and said salt indicates a plurality of distinguishing x-ray diffraction peaks at 2 Theta angles of 10-35 degrees as compared to non-distinguishing x-ray diffraction peaks at 2 Theta angles of greater than 35 degrees, wherein said distinguishing x-ray diffraction peaks have relative intensity counts between 500-1500 at 2 Theta angles of 10-35 degrees and non-distinguishing x-ray diffraction peaks have relative intensity counts of less than 500 at 2 Theta angles of greater than 35 degrees and no peaks are present with relative intensity accounts of more than 250 at 2 Theta angles between 35-60 degrees and wherein said salt has a particulate structure and an aspect ratio of 2:1 to 16:1.

2. A composition comprising the bis-quaternary pyridinium-2-aldoximine salt of claim 1, dispersed in a pharamaceutically acceptable carrier effective to therapeutically treat intoxication of a person or animal produced by a phosphorous containing cholinesterase inhibitor.

3. The bis-quaternary pyridinium-2-aldoximine salt of claim 1 combined in water in the form of an aqueous solution, suspension and/or emulsion.

4. The bis-quaternary pyridinium-2-aldoxime salt of claim 1 where R⁻ is a chlorine atom.

5. A bis-quaternary pyridinium-2-aldoxime salt of the formula:

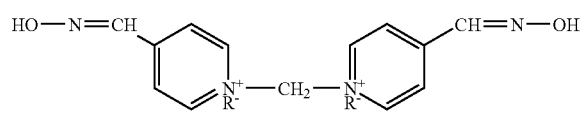

wherein R is a halogen and said salt indicates a plurality of distinguishing x-ray diffraction peaks at 2 Theta angles of 10-45 degrees as compared to non-distinguishing x-ray diffraction peaks at 2 Theta angles greater than 45 degrees, wherein said distinguishing x-ray diffraction peaks have relative intensity counts between 500-1500 at 2 Theta angles of 10-45 degrees and non-distinguishing x-ray diffraction peaks have relative intensity counts of less than 500 at 2 Theta angles of greater than 45 degrees and no peaks are present with relative intensity accounts of more than 250 at 2 Theta angles between 45-60 degrees and wherein said salt has a particulate structure comprising a square, rectangular, rhomboid or rhombus geometry.

6. A composition comprising the bis-quaternary pyridinium-2-aldoximine salt of claim 5, dispersed in a pharamaceutically acceptable carrier effective to therapeutically treat intoxication of a person or animal produced by a phosphorous containing cholinesterase inhibitor.

7. A composition comprising the bis-quaternary pyridinium-2-aldoximine salt of claim 5 combined in water in the form of an aqueous solution, suspension and/or emulsion.

8. The bis-quaternary pyridinium-2-aldoxime salt of claim 1 where R⁻ is a chlorine atom.

9. A bis-quaternary pyridinium-2-aldoxime salt comprising the formula:

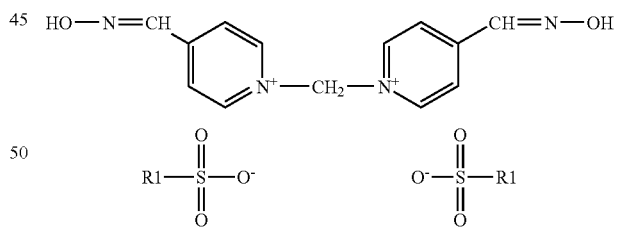

wherein R1 is a methyl and/or ethyl group and said salt indicates a plurality of distinguishing x-ray diffraction peaks at 2 Theta angles of 10-30 degrees as compared to non-distinguishing peaks at 2 Theta angles greater than 30 degrees and said salt has cubic rectangular crystal geometry, wherein said distinguishing x-ray diffraction peaks have relative intensity counts between 500-1500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 250 at 2 Theta angles between 30-60 degrees and wherein said salt has a particulate structure and an aspect ratio of 2:1 to 16:1 and wherein said salt has a particulate structure comprising cubic rectangular geometry.

10. The bis-quaternary pyridinium-2-aldoximine salt of claim 9, wherein R1 is a methyl group.

11. A composition comprising the bis-quaternary pyridinium-2-aldoximine salt of claim 9, dispersed in a pharamaceutically acceptable carrier effective to therapeutically treat intoxication of a person or animal produced by a phosphorous containing cholinesterase inhibitor.

12. A composition comprising the bis-quaternary pyridinium-2-aldoximine salt of claim 9 combined in water in the form of an aqueous solution, suspension and/or emulsion.

13. A bis-quaternary pyridinium-2-aldoxime salt of the formula:

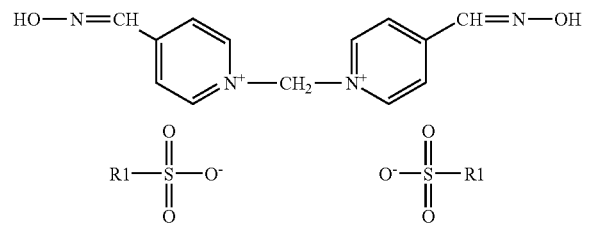

wherein R1 is a methyl and/or ethyl group and said salt indicates a plurality of distinguishing x-ray diffraction peaks at 2 Theta angles of 10-30 degrees as compared to non-distinguishing peaks at 2 Theta angles greater than 30 degrees and said salt has hexagonal crystal structure, wherein said distinguishing x-ray diffraction peaks have relative intensity counts between 1000-4500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 500 at 2 Theta angles between 35-60 degrees and wherein said salt has a particulate structure and an aspect ratio of 2:1 to 16:1 and wherein said salt has a particulate structure comprising hexagonal structure.

14. The bis-quaternary pyridinium-2-aldoximine salt of claim 13 wherein R1 is a methyl group.

15. A composition comprising the bis-quaternary pyridinium-2-aldoxime salt of claim 13, dispersed in a pharamaceutically acceptable carrier effective to therapeutically treat intoxication of a person or animal produced by phosphorous containing cholinesterase inhibitor.

16. A composition comprising the bis-quaternary pyridinium-2-aldoximine salt of claim 13 combined in water in the form of an aqueous solution, suspension and/or emulsion.

17. A method for preparing a bis-quaternary pyridinium-2-aldoxime salt comprising supplying pyridine-4-aldoximine of the formula:

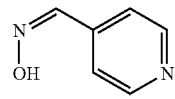

treating said pyridine-4-aldoximine with diodomethane to form 1,1'-methylenebis[4-[(hydroxyimino)methyl]-pyridinium] diodide of the following formula:

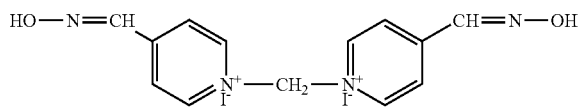

converting said 1,1'-methylenebis [4-[(hydroxyimino)methyl]-pyridinium] diodide to the following structure via ion exchange of the iodine to provide the following bis-quaternary pyridinium-2-aldoxime salt:

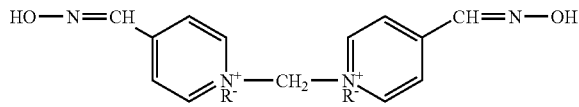

wherein R is a chlorine atom or an alkyl sulfonate group and where said alkyl sulfonate is of the general structure:

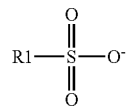

where R1 is a methyl or ethyl group and wherein said salt indicates one of the following:
when R is a chlorine atom said salt indicates a plurality of distinguishing x-ray diffraction peaks at 2 Theta angles of 10-35 degrees as compared to non-distinguishing x-ray diffraction peaks at 2 Theta angles of greater than 35 degrees, wherein said distinguishing x-ray diffraction peaks have relative intensity counts between 500-1500 at 2 Theta angles of 10-35 degrees and non-distinguishing x-ray diffraction peaks have relative intensity counts of less than 500 at 2 Theta angles of greater than 35 degrees and no peaks are present with relative intensity accounts of more than 250 at 2 Theta angles between 35-60 degrees and wherein said salt has a particulate structure and an aspect ratio of 2:1 to 16:1; or
when R is a chlorine atom, said salt indicates a plurality of distinguishing x-ray diffraction peaks at 2 Theta angles of 10-45 degrees as compared to non-distinguishing x-ray diffraction peaks at 2 Theta angles greater than 45 degrees, wherein said distinguishing x-ray diffraction peaks have relative intensity counts between 500-1500 at 2 Theta angles of 10-45 degrees and non-distinguishing x-ray diffraction peaks have relative intensity counts of less than 500 at 2 Theta angles of greater than 45 degrees and no peaks are present with relative intensity accounts of more than 250 at 2 Theta angles between 45-60 degrees and wherein said salt has a particulate structure comprising a square, rectangular, rhomboid or rhombus geometry; or
when R is said alkyl sulfonate group said salt indicates a plurality of distinguishing x-ray diffraction peaks at 2 Theta angles of 10-30 degrees as compared to non-distinguishing peaks at 2 Theta angles greater than 30 degrees and said salt has cubic rectangular crystal geometry, wherein said distinguishing x-ray diffraction peaks have relative intensity counts between 500-1500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 250 at 2 Theta angles between 30-60 degrees and wherein said salt has a particulate structure and an aspect ratio of 2:1 to 16:1 and wherein said salt has a particulate structure comprising cubic rectangular geometry; or when R is said alkyl sulfonate group said salt indicates a plurality of distinguishing x-ray diffraction peaks at 2 Theta angles of 10-30 degrees as compared to non-distinguishing peaks at 2 Theta angles greater than 30 degrees and said salt has hexagonal crystal structure, wherein said distinguishing x-ray diffraction peaks have relative intensity counts between 1000-4500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 500 at 2 Theta angles between 35-60 degrees and wherein said salt has a particulate structure and an aspect ratio of 2:1 to 16:1 and wherein said salt has a particulate structure comprising hexagonal structure.

18. The method of claim 17 wherein R1 is a methyl group.

19. The method of claim 17 wherein said bis-quaternary pyridinium-2-aldoxime salt is dispersed in a pharmaceutically acceptable carrier effective to therapeutically treat intoxication of a person or animal produced by a phosphorous containing cholinesterase inhibitor.

20. The method of claim 17 wherein said bis-quaternary pyridinium-2-aldoxime salt is combined in water and forming an aqueous solution, suspension and/or emulsion.

21. A therapeutic method of treating a person or animal for intoxication with a phosphorous containing cholinesterase inhibitor, comprising administering to a person or animal one or more of the following compounds:
(i) a bis-quaternary pyridinium-2-aldoxime salt of the formula:

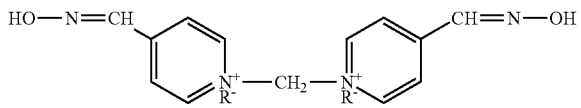

wherein R is a halogen and said salt indicates a plurality of distinguishing x-ray diffraction peaks at 2 Theta angles of 10-35 degrees as compared to non-distinguishing x-ray diffraction peaks at 2 Theta angles of greater than 35 degrees, wherein said distinguishing x-ray diffraction peaks have relative intensity counts between 500-1500 at 2 Theta angles of 10-35 degrees and non-distinguishing x-ray diffraction peaks have relative intensity counts of less than 500 at 2 Theta angles of greater than 35 degrees and no peaks are present with relative intensity accounts of more than 250 at 2 Theta angles between 35-60 degrees and wherein said salt has a particulate structure and an aspect ratio of 2:1 to 16:1; or (ii) a bis-quaternary pyridinium-2-aldoxime salt of the formula:

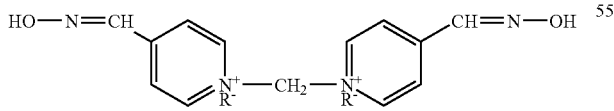

wherein R is a halogen and said salt indicates a plurality of distinguishing x-ray diffraction peaks at 2 Theta angles of 10-45 degrees as compared to non-distinguishing x-ray diffraction peaks at 2 Theta angles greater than 45 degrees, wherein said distinguishing x-ray diffraction peaks have relative intensity counts between 500-1500 at 2 Theta angles of 10-45 degrees and non-distinguishing x-ray diffraction peaks have relative intensity counts of less than 500 at 2 Theta angles of greater than 45 degrees and no peaks are present with relative intensity accounts of more than 250 at 2 Theta angles between 45-60 degrees and wherein said salt has a particulate structure comprising a square, rectangular, rhomboid or rhombus geometry; or (iii) a bis-quaternary pyridinium-2-aldoxime salt of the formula:

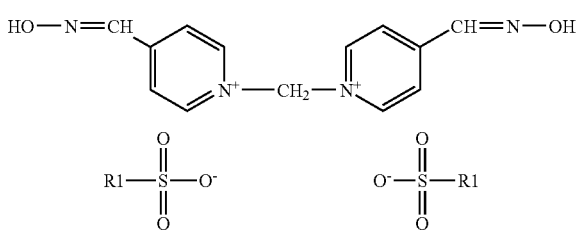

wherein R1 is a methyl and/or ethyl group and said salt indicates a plurality of distinguishing x-ray diffraction peaks at 2 Theta angles of 10-30 degrees as compared to non-distinguishing peaks at 2 Theta angles greater than 30 degrees and said salt has cubic rectangular crystal geometry, wherein said distinguishing x-ray diffraction peaks have relative intensity counts between 500-1500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 250 at 2 Theta angles between 30-60 degrees and wherein said salt has a particulate structure and an aspect ratio of 2:1 to 16:1 and wherein said salt has a particulate structure comprising cubic rectangular geometry; or (iv) a bis-quaternary pyridinium-2-aldoxime salt of the formula:

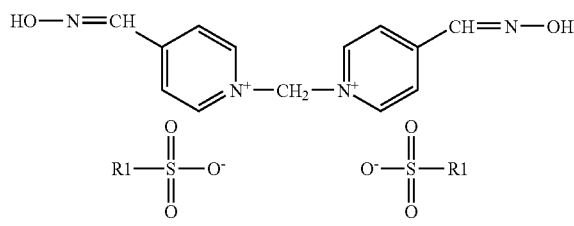

wherein R1 is a methyl and/or ethyl group and said salt indicates a plurality of distinguishing x-ray diffraction peaks at 2 Theta angles of 10-30 degrees as compared to non-distinguishing peaks at 2 Theta angles greater than 30 degrees and said salt has hexagonal crystal structure, wherein said distinguishing x-ray diffraction peaks have relative intensity counts between 1000-4500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 500 at 2 Theta angles between 35-60 degrees and wherein said salt has a particulate structure and an aspect ratio of 2:1 to 16:1 and wherein said salt has a particulate structure comprising hexagonal structure.

22. The therapeutic method of claim 21, wherein R1 in the bis-quaternary puridinium-2-aldoxime salt, having either cubic rectangular crystal structure or hexagonal crystal structure is a methyl group.

* * * * *